(12) United States Patent
Lyons et al.

(10) Patent No.: US 6,998,391 B2
(45) Date of Patent: Feb. 14, 2006

(54) METHOD FOR TREATING DISEASES ASSOCIATED WITH ABNORMAL KINASE ACTIVITY

(75) Inventors: John Lyons, Moraga, CA (US); Joseph Rubinfeld, Danville, CA (US)

(73) Assignee: SuperGen.Inc., Dublin, CA (US)

(*) Notice: Subject to any disclaimer, the term of this patent is extended or adjusted under 35 U.S.C. 154(b) by 0 days.

(21) Appl. No.: 10/206,854

(22) Filed: Jul. 26, 2002

(65) Prior Publication Data

US 2004/0127453 A1 Jul. 1, 2004

Related U.S. Application Data

(63) Continuation-in-part of application No. 10/071,849, filed on Feb. 7, 2002, now abandoned.

(51) Int. Cl.
*A61K 31/7072* (2006.01)

(52) U.S. Cl. .......................... 514/49; 514/85; 514/269; 514/234.5; 514/300; 536/23.5; 536/23.1; 435/69.1; 435/325; 530/350; 424/45; 424/450

(58) Field of Classification Search .................. 514/49, 514/65, 269, 234.5, 300; 536/23.5, 23.1; 435/69.1, 325; 530/350; 424/45, 450
See application file for complete search history.

(56) References Cited

U.S. PATENT DOCUMENTS

| 2001/0044451 A1 | 11/2001 | Fraley et al. | 514/300 |
| 2001/0047007 A1 | 11/2001 | Fraley et al. | 514/300 |

FOREIGN PATENT DOCUMENTS

| WO | WO 02/069903 | 9/2002 |

OTHER PUBLICATIONS

U.S. Appl. No. 10/071,849, filed on Feb. 7, 2002.*
Kantarjian et al. "Treatment of accelerated phase of Philadelphia chromosome positive chronic leukemia with imatinib mesylate". Conference abstract Blood, vol. 98, No. 11, Part 1, p. 141a, 2001.*

Von Hoff et al. "%–azacytidine. A new anticancer drug with effectiveness in acute myelogenous leukemia." Annals of Internal Medicine, 85(2), pp. 237–245, 1976.*

Sheikhnejad, G. et al., "Mechanism of inhibition of DNA (cytosine C5)–methyltransferases by oligodeoxyribonucleotides containing 5,6–dihydro–5–azacytosine", *J. Mol. Biol.*, 1999, pp. 2021–2034, vol. 285.

Goffin, J. et al., "DNA methyltransferase inhibitors—state of the art", *Annals of Oncology*, 2002, pp. 1699–1716, vol. 13.

Wijermans, P. et al., "Low–dose 5–aza–2'–deoxycytidine, a DNA hypomethylating agent, for the treatment of high–risk myelodysplastic syndrome: a multicenter phase II study in elderly patients", *Journal of Clinical Oncology*, Mar. 2000, pp. 956–962, vol. 18, No. 5.

* cited by examiner

*Primary Examiner*—James O. Wilson
*Assistant Examiner*—Devesh Khare
(74) *Attorney, Agent, or Firm*—Wilson, Sonsini, Goodrich & Rosati

(57) ABSTRACT

Methods are provided for treating diseases associated with abnormal activity of kinases. The method comprises: administering a DNA methylation inhibitor to the patient in therapeutically effective amount; and administering a kinase inhibitor to the patient in therapeutically effective amount, such that the in vivo activity of the kinase is reduced relative to that prior to the treatment. The method can be used to treat cancer associated with abnormal activity of kinases such as phosphatidylinositol 3'-kinase (PI3K), protein kinases including serine/threonine kinases such as Raf kinases, protein kinase kinases such as MEK, and tyrosine kinases such as those in the epidermal growth factor receptor family (EGFR), platelet-derived growth factor receptor family (PDGFR), vascular endothelial growth factor receptor (VEGFR) family, nerve growth factor receptor family (NGFR), fibroblast growth factor receptor family (FGFR) insulin receptor family, ephrin receptor family, Met family, Ror family, c-kit family, Src family, Fes family, JAK family, Fak family, Btk family, Syk/ZAP-70 family, and Abl family.

20 Claims, No Drawings

SEQUENCE LISTING

<160> NUMBER OF SEQ ID NOS: 1

<210> SEQ ID NO 1
<211> LENGTH: 8
<212> TYPE: PRT
<213> ORGANISM: Artificial Sequence

```
-continued

<220> FEATURE:
<223> OTHER INFORMATION: Inhibitor of Non-Receptor Tyrosine Kinase from
                        the Syk/ZAP-70 family

<400> SEQUENCE: 1

Lys Leu Ile Leu Phe Leu Leu Leu
1               5
```

METHOD FOR TREATING DISEASES ASSOCIATED WITH ABNORMAL KINASE ACTIVITY

CROSS-REFERENCE TO RELATED APPLICATIONS

This application is a continuation-in-part of U.S. patent application Ser. No. 10/071,849 entitled "Method for Treating Chronic Myelogenous Leukemia" filed on Feb. 7, 2002. The above application is incorporated herein by reference.

BACKGROUND OF THE INVENTION

1. Field of the Invention

The invention relates to methods, compositions, and kits for treating diseases associated with abnormal protein kinase activity, and more particularly for treating cancer associated with abnormal protein tyrosine kinase activity, such as chronic myelogenous leukemia.

2. Description of Related Art

Chronic Myelogenous Leukemia (CML) is a myeloproliferative disorder of a pluripotent hematopoietic stem cell with a particular cytogenetic abnormality, the Philadelphia chromosome. Faderl et al (1999) Ann. Intern. Med. 131: 207–219. In childhood, it accounts for only 2 to 5% of all malignant disorders and presents as either of two distinct clinical entities, adult-type CML and juvenile CML. Adult-type CML of childhood is indistinguishable from that seen in older patients. However, juvenile CML is restricted to children and is Philadelphia chromosome negative. Grier and Civin (1998) in (Nathan and Oski, eds) Hematology of Infancy and Childhood, volume 2, 5th ed, W. B. Saunders Company, 34:1286–1459.

CML is a progressive, uniformly fatal disease in untreated patients. It is characterized by three distinct phases: a chronic phase lasting three to five years; an acute or accelerated phase lasting three to six months; and a brief blastic crisis phase. The progression of the disease to blast crisis results in rapid death due to infections, bleeding and leukemic organ infiltration.

Philadelphia chromosome, the characteristic cytogenetic abnormality of CML, results from a reciprocal chromosomal translocation, t(9;22)(q34;q11), in a hematopoietic stem cell. This translocation produces a fusion gene, termed Bcr-Abl, created by the juxtaposition of the abelson murine leukemia (Abl) protooncogene on chromosome 9 with a portion of the breakpoint cluster region (Bcr) gene on chromosome 22. The Bcr-Abl fusion protein's leukomogenic potential is derived from its constitutively activated tyrosine kinase activity, which causes a perturbation of stem cell function through unclear mechanisms. This activity results in interference with basic cellular processes, such as control of proliferation, adherence, and physiological death. More advanced stages of CML are also characterized by aberrant methylation of multiple genes, including the p15/Ink-4b cell-cycle regulator gene. Cortes et al (1997) Baillieres Clin Haematol 10(2):277–90. Aberrations in DNA methylation, whether general or site specific, are common in cancer and have important roles in tumor initiation, progression and resistance. Lubbert et al (2001) Br J Haematol 114(2): 349–357.

Until recently, standard therapy for chronic phase CML consisted of conventional chemotherapy, interferon-alpha (with or without Ara-C), donor lymphocyte infusions and allergenic bone marrow transplantation, each offering different risk-benefit trade-offs.

Overall, available data suggests the view that allergenic bone marrow transplantation offers to eligible patients (children and young adults with an human leukocyte antigen-matched sibling donor) their best prospect for cure. However, bone marrow transplantation has certain limitations i.e., the availability of a suitable donor (10–40%), the risk of graft-vs.-host disease (8–60%) and a high rate of transplant-related mortality (20–40%).

Long-term follow-up of patients treated in large-scale randomized trials utilizing one or two of the above therapeutic modalities has shown a significant correlation between cytogenetic responses and prolonged survival. Silver et al (1999) Blood 94:1517–1536.

Imatinib mesylate is one of the recent therapeutic breakthroughs in the treatment of CML. Imatinib mesylate is a small molecule inhibitor of tyrosine kinase activity that results in a high response rate in CML. In the pivotal Phase II studies, nearly all patients (88%) with chronic phase CML achieved a complete hematologic response, and nearly half (49%) had a major cytogenetic response. Imatinib mesylate produced remissions in 63% of accelerated phase CML patients and 26% of blast phase patients. A complete cytogenetic response was seen in 30% of chronic phase CML, 14% of accelerated phase CML, and 5% of blast phase CML patients and was maintained for four weeks in 16%, 4%, and 1%, respectively. Novartis, Gleevec package insert T-2001-14 90012401.

Imatinib mesylate was approved by the FDA in May 2001 for the treatment of CML in all phases (after failure of interferon in the chronic phase). However, in blast phase CML, the responses to imatinib mesylate are usually of very short duration, and most patients manifest resistant/refractory disease within six months of therapy. Druker et al (2001) N. Engl. J. Med. 344: 1038–1042. Resistance to imatinib mesylate was associated with reactivation of Bcr-Abl and could be conferred by a single point substitution of threonine for isoleucine in the tyrosine kinase. Gorre et al (2001) Science 293: 2163. Consequently, there exists a need for compositions and methods for treating CML patients who are resistant to imatinib mesylate.

SUMMARY OF THE INVENTION

The present invention provides compositions, kits and methods for treat a host, preferably human, having or predisposed to a disease associated with abnormal activity of protein kinase. In general, a DNA methylation inhibitor is administered to the host in combination with a protein kinase inhibitor such that the onset or progression of the disease is retarded. The DNA methylation inhibitor may exert its therapeutic effect(s) via reestablishment of transcriptional activity of disease-suppressing genes which may further inhibit the activity of the protein kinase. By using such a combination therapy, the activity of not only the protein kinase itself but also other proteins which participate in the upstream or downstream signal transduction of the protein kinase may be efficiently and synergistically inhibited by controlling expression of genes encoding these proteins through DNA hypomethylation, thus leading to more efficacious treatment of the disease.

In one aspect of the present invention, a method is provided for treating a patient with a protein tyrosine kinase inhibitor imatinib mesylate in combination with a DNA methylation inhibitor. The method is preferably directed to a patient that has a degree of resistance to imatinib mesylate, the resistance being mitigated by the administration of the DNA methylation inhibitor. In particular, the method is directed to treating a disease state associated with activity of protein tyrosine kinase such as oncoprotein Bcr-Abl involved in chronic myelogenous leukemia (CML), platelet-derived growth factor (PDGF) receptor involved in prostate cancer and glioblastoma, and c-Kit involved in gastrointestinal stromal tumor (GIST) and small cell lung cancer (SCLC), as well as other types of cancer, where the combination treatment using imatinib mesylate and a DNA methylation inhibitor is synergistic.

In one embodiment, the method comprises: administering to the patient imatinib mesylate and a DNA methylation inhibitor.

In another embodiment, the method comprises: administering to the patient having chronic myelogenous leukemia imatinib mesylate and a DNA methylation inhibitor.

In another embodiment, a method is provided for treating a patient having chronic myelogenous leukemia comprising: administering to a patient having chronic myelogenous leukemia and a degree of resistance to imatinib mesylate, a therapeutically effective amount of a DNA methylation inhibitor which mitigates the imatinib mesylate resistance.

In one variation, the patient has already manifested resistance to imatinib mesylate within 6 months of the treatment with imatinib mesylate as defined by no improvement in the prognosis or worsening of the prognosis.

In another aspect of the invention, a method is provided for treating a CML patient who is intolerant of imatinib mesylate treatment. The method comprises: administering to a patient having chronic myelogenous leukemia and manifesting intolerance to imatinib mesylate, a therapeutically effective amount of a DNA methylation inhibitor which mitigates the imatinib mesylate intolerance or the CML phenotype.

In one variation, the patient has already manifested intolerance to imatinib mesylate within 6 months of the treatment with imatinib mesylate as defined by manifesting a symptom selected from the group consisting of hepatoxicity, fluid retention syndrome, neutropenia, hemorrhage, dyspepsia, dyspnea, diarrhea, muscle cramps, skin rash, fatigue, headache, nausea, vomiting, and thrombocytopenia.

In yet another aspect of the invention, a method is provided for treating a patient having chronic myelogenous leukemia and resistant to imatinib mesylate treatment. The method comprises: administering to the patient imatinib mesylate and a DNA methylation inhibitor such that the patient's resistance to imatinib mesylate in the absence of the DNA methylation inhibitor is reduced.

In another embodiment, a method is provided for treating a patient having chronic myelogenous leukemia, comprising: administering to a patient in blast phase of chronic myelogenous leukemia a therapeutically effective amount of a DNA methylation inhibitor.

According to any of the above methods for treating chronic myelogenous leukemia, the patient's chronic myelogenous leukemia is optionally staged prior to administration. Staging the patient having chronic myelogenous leukemia optionally includes determining the number of blasts, promyelocytes, basophil, and platelets per liter of peripheral blood or bone marrow. Optionally, staging the patient having chronic myelogenous leukemia may include counting of the concentration of BCR/Abl positive cells in bone marrow and/or peripheral blood.

Also according to any of the above methods for treating chronic myelogenous leukemia, the DNA methylation inhibitor is optionally administered to the patient in the blast, chronic or accelerated phase of chronic myelogenous leukemia. In one variation, the method is performed when the patient in blast phase of chronic myelogenous leukemia has more than 30% blasts in peripheral blood or bone marrow.

Also according to any of the above methods for treating chronic myelogenous leukemia, the DNA methylation inhibitor may be administered by a variety of routes, including but not limited to orally, parenterally, intraperitoneally, intravenously, intraarterially, transdermally, sublingually, intramuscularly, rectally, transbuccally, intranasally, liposomally, via inhalation, vaginally, intraoccularly, via local delivery, subcutaneously, intraadiposally, intraarticularly, or intrathecally.

According to any of the above methods, it is noted that administering imatinib mesylate and the DNA methylation inhibitor to the patient may comprise administering imatinib mesylate to the patient for a period of time prior to the administration of the DNA methylation inhibitor, administering the DNA methylation inhibitor to the patient for a period of time prior to the administration of imatinib mesylate, or initiating administration of the DNA methylation inhibitor and imatinib mesylate to the patient at the same time. It is noted that the method may also comprise administering imatinib mesylate and the DNA methylation inhibitor to the patient at the same time for at least a portion of the time that the drugs are administered.

According to any of the above methods, in one variation, imatinib mesylate is administered to the patient at a dose of 100–800 mg/day, optionally at a dose of 200–400 mg/day, and optionally at a dose of 500–800 mg/day. Such administrations may optionally last for a period of at least 2, 4, 6, 8, 10 or more days.

Also according to any of the above methods, in one variation, the DNA methylation inhibitor is administered to the patient via an intravenous infusion per day at a dose ranging from 1 to 100 mg/m$^2$, optionally at a dose ranging from 2 to 50 mg/m$^2$, and optionally at a dose ranging from 5 to 20 mg/m$^2$.

Also according to any of the above methods, in one variation, the DNA methylation inhibitor is administered to the patient subcutaneously at a dose ranging from 0.01 to 1 mg/Kg, optionally at a dose ranging from 0.1 to 0.5 mg/Kg at least once a week for at least 4 weeks, optionally at a dose ranging from 0.1 to 0.3 mg/Kg twice a week for at least 4 weeks, and optionally at a dose of 0.2 mg/Kg twice a week for 6 weeks, drug-free for two weeks, and then at a dose of 0.2 mg/Kg twice a week until the clinical endpoint(s) is achieved.

Also according to any of the above methods, the DNA methylation inhibitor may optionally be a cytidine analog such as cytosine arabinoside. In one variation, the cytidine analog is decitabine.

In one particular variation, the DNA methylation inhibitor is decitabine and is administered intravenously or subcutaneously. In a further particular variation, decitabine is administered to the patient via an intravenous infusion per day at a dose ranging from 1 to 100 mg/m$^2$, optionally ranging from 2 to 50 mg/m$^2$ and optionally ranging from 5 to 20 mg/m$^2$.

In one example, decitabine is administered to the patient via an intravenous infusion per day for at least 3 days per treatment cycle at a dose ranging from 1 to 100 mg/m$^2$. In a further example, decitabine is administered to the patient via an intravenous infusion at a dose ranging from 5 to 20 mg/m$^2$ for 1 hour per day for 5 consecutive days for 2 weeks per treatment cycle.

Compositions are also provided. In one embodiment, a composition is provided that comprises a DNA methylation inhibitor and imatinib mesylate. The DNA methylation inhibitor may optionally be a cytidine analog such as cytosine arabinoside. In one variation, the cytidine analog is decitabine. In another variation, the composition is formulated for intravenous, inhalation, oral, or subcutaneous administration.

In yet another aspect of the invention, a method is provided for treating a disease associated with abnormal activity of a kinase in vivo. The method comprises: administering a DNA methylation inhibitor to a patient having a disease associated with abnormal activity of a kinase in vivo; and administering a kinase inhibitor to the patient. The DNA methylation inhibitor and the kinase inhibitor are administered in therapeutically effective amounts, preferably in therapeutically effective and synergistic amounts.

The kinase may be an enzyme that can catalyze phosphorylation of a molecule such as a protein or a nucleic acid. Preferably, the kinase may be a protein kinase such as a tyrosine kinase, a serine/threonine kinase and a protein kinase kinase.

The disease associated with abnormal kinase activity may be any pathological condition that is directly or indirectly caused by elevated levels or enhanced enzymatic activity of kinase as compared with those indexes under a normal physiological condition. Examples of the pathological condition include but are not limited to inflammation, benign tumors, malignant tumors, leukemia, asthma, allergy-associated chronic rhinitis, autoimmune diseases and mastolocytosis. Particularly, the pathological condition is cancer.

The DNA methylation inhibitor may be a cytidine analog such as cytosine arabinoside and decitabine. Particularly, the DNA methylation inhibitor is decitabine.

The DNA methylation inhibitor may be administered orally, parenterally, intraperitoneally, intravenously, intraarterially, transdermally, sublingually, subcutaneously, intramuscularly, rectally, transbuccally, intranasally, liposomally, via inhalation, vaginally, intraoccularly, via local delivery, subcutaneously, intraadiposally, intraarticularly, or intrathecally.

In a preferred embodiment, the DNA methylation inhibitor is decitabine and is administered intravenously, intramuscularly, subcutaneously, orally, or via inhalation.

The kinase inhibitor may be in a form of chemical compound, protein, peptide, enzyme, antibody, antisense fragment, antisense fragment linked to enzyme, or antisense fragment linked to peptide.

The kinase inhibitor may be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery, subcutaneously, intraadiposally, intraarticularly, or intrathecally.

The kinase inhibitor may inhibit the enzymatic activity or gene expression activity of a kinase. Gene expression activity of a kinase includes, but is not limited to, transcriptional activity such as binding of transcription factor(s) to the promoter region of the kinase gene and transcribing mRNA, translational activity such as production of the kinase, and post-translational activity such as proteolytic processing of the precursor of the kinase, and differential expression of endogenenous inhibitors of the kinase.

In one variation, the kinase is a serine/threonine kinase such as a Raf kinase; and the kinase inhibitor is BAY 43-9006.

In another variation, the kinase is a protein kinase kinase such as an Raf-mitogen-activated protein kinase kinase (MEK) and protein kinase B (Akt) kinase.

In yet another variation, the kinase is an extracellular signal-regulated kinase (ERK). Examples of the inhibitor of ERK include but are not limited to PD98059, PD184352, and U0126.

In yet another variation, the kinase is a phosphatidylinositol 3'-kinase (PI3K). Examples of the inhibitor of PI3K include but are not limited to LY294002.

In a particular variation, the kinase is a tyrosine kinase. The tyrosine kinase may be a receptor tyrosine kinase and non-receptor tyrosine kinase.

Examples of the receptor tyrosine kinase include, but are not limited to, epidermal growth factor receptor family (EGFR), platelet-derived growth factor receptor (PDGFR) family, vascular endothelial growth factor receptor (VEGFR) family, nerve growth factor receptor (NGFR) family, fibroblast growth factor receptor family (FGFR) insulin receptor family, ephrin receptor family, Met family, and Ror family.

Examples of the epidermal growth factor receptor family include, but are not limited to, HER1, HER2/neu, HER3, and HER4.

Examples of the inhibitors of epidermal growth factor receptor family include, but are not limited to, HERCEPTIN®, ZD1839 (IRESSA®), PD168393, CI1033, IMC-C225, EKB-569, and inhibitors binding covalently to Cys residues of the receptor tyrosine kinase.

Examples of diseases associated with abnormal activity of the epidermal growth factor receptor family, include, but are not limited to, epithelial tumor, carcinoma, carcinoma of upper aerodigestive tract, lung cancer, and non-small cell lung cancer.

Examples of the vascular endothelial growth factor receptor family include, but are not limited to, VEGFR1, VEGFR2, and VEGFR3.

An example of the inhibitor of the vascular endothelial growth factor receptor family includes, but is not limited to, SU6668.

Examples of the disease associated with abnormal activity of the vascular endothelial growth factor receptor family include, but are not limited to, solid and metastasis-prone tumors.

Examples of the nerve growth factor receptor family include, but are not limited to, trk, trkB and trkC.

Examples of the inhibitors of the nerve growth factor receptor family include, but are not limited to, CEP-701, CEP-751, and indocarbazole compound.

Examples of the diseases associated with abnormal activity of the nerve growth factor receptor family include, but are not limited to, prostate, colon, papillary and thyroid cancers, neuromas and osteoblastomas.

Examples of the Met family include, but are not limited to, Met, TPR-Met, Ron, c-Sea, and v-Sea.

Examples of disease associated with activity of the receptor tyrosine kinase from Met family include, but are not limited to, invasively in-growing tumor, carcinoma, papillary carcinoma of thyroid gland, colon, carcinoma, renal carcinoma, pancreatic carcinoma, ovarian carcinoma, head and neck squamous carcinoma.

Examples of the non-receptor tyrosine kinase include, but are not limited to, c-kit family, Src family, Fes family, JAK family, Fak family, Btk family, Syk/ZAP-70 family, and Abl family.

Examples of the non-receptor tyrosine kinases from the Src family include, but are not limited to, Src, c-Src, v-Src, Yes, c-Yes, v-Yes, Fyn, Lyn, Lck, Blk, Hck, Fgr, c-Fgr, v-Fgr, p56lck, Tk1, Csk, and Ctk.

Examples of the inhibitors of the non-receptor tyrosine kinase from the Src family include, but are not limited to, SU101 and CGP 57418B.

Examples of the diseases associated with activity of the non-receptor tyrosine kinase from the Src family include, but are not limited to, breast cancer, carcinoma, myeloma, leukemia, and neuroblastoma.

Examples of the non-receptor tyrosine kinases from the Fes family include, but are not limited to, c-fes/fps, v-fps/fes, p94-c-fes-related protein, and Fer.

Examples of the diseases associated with activity of the non-receptor tyrosine kinase from the Fes family include, but are not limited to, tumor of mesenchymal origin and tumor of hematopoietic origin.

Examples of the non-receptor tyrosine kinases from the JAK family include, but are not limited to, Jak1, Jak2, Tyk2, and Jak3.

Examples of the inhibitors of the non-receptor tyrosine kinase from the JAK family include, but are not limited to, tyrphostin, member of CIS/SOCS/Jab family, synthetic component AG490, dimethoxyquinazoline compound, 4-(phenyl)-amino-6,7-dimethoxyquinazoline, 4-(4'-hydroxyphenyl)-amino-6,7-dimethoxyquinazoline, 4-(3'-bromo-4'-hydroxylphenyl)-amino-6,7-dimethoxyquinazoline, and 4-(3',5'-dibromo-4'-hydroxylphenyl)-amino-6,7-dimethoxyquinazoline.

Examples of the diseases associated with activity of the non-receptor tyrosine kinase from JAK family include, but are not limited to, tumor of mesenchymal origin and tumor of hematopoietic origin.

Examples of the non-receptor tyrosine kinases from the Fak family include, but are not limited to, Fak and CAKβ/Pyk2/RAFTK.

Examples of the inhibitors of the non-receptor tyrosine kinases from the Fak family include, but are not limited to, a dominant negative mutant S1034-FRNK; a metabolite FTY720 from Isaria sinclarii, and FAK antisense oligonucleotide ISIS 15421.

Examples of the diseases associated with abnormal activity of the non-receptor tyrosine kinases from Fak family include, but are not limited to, human carcinoma, metastasis-prone tumor, and tumor of hematopoietic origin.

Examples of the non-receptor tyrosine kinase from the Btk family include, but are not limited to, Btk/Atk, Itk/Emt/Tsk, Bmx/Etk, and Itk, Tec, Bmx, and Rlk.

Examples of the inhibitors of the non-receptor tyrosine kinases from Btk family include, but are not limited to, alpha-cyano-beta-hydroxy-beta-methyl-N-(2,5-dibromophenyl)propenamide.

Examples of the diseases associated with abnormal activity of the non-receptor tyrosine kinase from the Btk family include, but are not limited to, B-lineage leukemia and lymphoma.

Examples of the non-receptor tyrosine kinases from the Syk/ZAP-70 family include, but are not limited to, Syk and ZAP-70.

Examples of the inhibitors of the non-receptor tyrosine kinases from the Syk/ZAP-70 family include, but are not limited to, piceatannol, 3,4-dimethyl-10-(3-aminopropyl)-9-acridone oxalate, acridone-related compound, Lys-Leu-Ile-Leu-Phe-Leu-Leu-Leu [SEQ ID NO: 1] peptide, and peptide containing Lys-Leu-Ile-Leu-Phe-Leu-Leu-Leu motif.

Examples of the diseases associated with abnormal activity of the non-receptor tyrosine kinases from the Syk/ZAP-70 family include, but are not limited to, benign breast cancer, breast cancer, and tumor of mesenchymal origin.

DETAILED DESCRIPTION OF THE INVENTION

In general, the present invention provides novel therapeutics and methods for treating diseases associated with abnormal cell proliferation caused by activation of oncogenes and/or suppression of tumor suppressors. In particular, methods are provided for treating a disease state associated with activity of protein tyrosine kinase such as oncoprotein Bcr-Abl involved in chronic myelogenous leukemia (CML), platelet-derived growth factor (PDGF) receptor involved in prostate cancer and glioblastoma, and c-Kit involved in gastrointestinal stromal tumor (GIST) and small cell lung cancer (SCLC), as well as other types of cancer. In general, a DNA methylation inhibitor is administered to the host in combination with a protein kinase inhibitor such that the onset or progression of the disease is retarded. The DNA methylation inhibitor may exert its therapeutic effect(s) via reestablishment of transcriptional activity of disease-suppressing genes which may further inhibit the activity of the protein kinase. By using such a combination therapy, the activity of not only the protein kinase itself but also other proteins which participate in the upstream or downstream signal transduction of the protein kinase may be efficiently and synergistically inhibited by controlling expression of genes encoding these proteins through DNA hypomethylation, thus leading to more efficacious treatment of the disease.

In one aspect of the present invention, a monotherapy with a DNA methylation inhibitor is provided for treating a CML patient who has a degree of resistance to imatinib mesylate, especially in accelerated or blast phase of CML. This monotherapy may also be used to treat patients having other diseases but manifesting resistance to the treatment of imatinib mesylate.

In another aspect of the present invention, a combination therapy is provided for treating various types of cancer associated with protein tyrosine kinase activity, such as CML, prostate cancer, glioblastoma, GIST and SCLC.

The inventors believe that a DNA methylation inhibitor such as decitabine should reactivate certain genes which participate in the pathways of protein tyrosine kinase but with their functions effected by methylation, presumably in the promoter regions. Loss of these gene functions could lead to elevated expression and/or activity of protein tyrosine kinase, resulting worse prognosis of the disease. Since imatinib mesylate has a strong inhibitory effect on protein tyrosine kinase activity, a treatment combining the use of imatinib mesylate and decitabine would have a synergistic effect via targeting different genes in converging or diverging signal transduction pathways. Further, lower doses of these two drugs may be used in the combination therapy to reduce side effects associated with the monotherapy with either one of these two drugs.

1. Imatinib Mesylate

Imatinib mesylate is a protein tyrosine kinase inhibitor that inhibits the Bcr-Abl tyrosine kinase created by the Philadelphia chromosome abnormality in CML. Imatanib mesylate achieves this inhibitory result through binding to the adenosine triphosphate-binding site of the Bcr-Abl tyrosine kinase, which prevents phosphorylation of substrates and related malignant transformation. Through inhibition of this kinase, it is believed that imatinib mesylate inhibits cell proliferation and induces apoptosis. T. Schindler et al (2000) Science 289:1938–1942.

Imatinib mesylate is indicated for treatment of CML patients in blast phase, accelerated phase, or in chronic phase after failure of interferon-alpha therapy. Present dosages recommended for treatment with imatinib mesylate are 400 mg/day for patients with chronic phase CML and 600 mg/day for patients with accelerated phase or blast phase CML. In the event of disease progression, failure to achieve a satisfactory hematologic response after at least 3 months of treatment; or loss of a previously achieved hematologic response, the dose of imatinib mesylate may be increased. Treatment dosage may be increased in patients with chronic phase CML from 400 mg/day to 600 mg/day in the absence of severe adverse drug reaction and severe non-leukemia related neutropenia or thrombocytopenia. Similarly, treatment dosage may be increased in patients with chronic phase CML from 600 mg/day to 800 mg/day. Novartis, Gleevec package insert T-2001-14 90012401.

However, many CML patients do not respond or lose response to treatment with imatinib mesylate. This is particularly the case in blast phase CML, the responses to imatinib mesylate are usually of very short duration, and most patients manifest resistant/refractory disease within six months of therapy. Druker et al (2001) N. Engl. J. Med. 344: 1038–1042. According to the present invention, it is believed that DNA methylation inhibitors can be used to treat CML patients that are resistant to the treatment with imatinib mesylate.

2. DNA Methylation Inhibitors

Decitabine, 5-aza-2'-deoxycytidine, is an antagonist of its related natural nucleoside, deoxycytidine. The only structural difference between these two compounds is the presence of a nitrogen at position 5 of the cytosine ring in decitabine as compared to a carbon at this position for deoxycytidine. Two isomeric forms of decitabine can be distinguished. The β-anomer is the active form. The modes of decomposition of decitabine in aqueous solution are (a) conversion of the active α-anomer to the inactive β-anomer (Pompon et al. (1987) J. Chromat. 388:113–122); (b) ring cleavage of the aza-pyrimidine ring to form N-(formylamidino)-N'-β-D-2'-deoxy-(ribofuranosy)-urea (Mojaverian and Repta (1984) J. Pharm. Pharmacol. 36:728–733); and (c) subsequent forming of guanidine compounds (Kissinger and Stemm (1986) J. Chromat. 353:309–318).

Decitabine possesses multiple pharmacological characteristics. At a molecular level, it is capable of specifically inhibiting cell growth at S phase and DNA methylation. At a cellular level, decitabine can induce cell differentiation and exert hematological toxicity. Despite having a short half life in vivo, decitabine has excellent tissue distribution.

The most prominent function of decitabine is its ability to specifically and potently inhibit DNA methylation. For example, in the methylation of cytosine in CpG islands, methylation of cytosine to 5-methylcytosine occurs at the level of DNA. Inside the cell, decitabine is first converted into its active form, the phosphorylated 5-aza-deoxycytidine, by deoxycytidine kinase which is primarily synthesized during the S phase of the cell cycle. The affinity of decitabine for the catalytical site of deoxycytidine kinase is similar to the natural substrate, deoxycytidine. Momparler et al. (1985) 30:287–299. After conversion to its triphosphate form by deoxycytidine kinase, decitabine is incorporated into replicating DNA at a rate similar to that of the natural substrate, dCTP. Bouchard and Momparler (1983) Mol. Pharmacol. 24:109–114.

Incorporation of decitabine into the DNA strand has a hypomethylation effect. Each class of differentiated cells has its own distinct methylation pattern. After chromosomal duplication, in order to conserve this pattern of methylation, the 5-methylcytosine on the parental strand serves to direct methylation on the complementary daughter DNA strand. Substituting the carbon at the 5 position of the cytosine for a nitrogen interferes with this normal process of DNA methylation. The replacement of 5-methylcytosine with decitabine at a specific site of methylation produces an irreversible inactivation of DNA methyltransferase, presumably due to formation of a covalent bond between the enzyme and decitabine. Juttermann et al. (1994) Proc. Natl. Acad. Sci. USA 91:11797–11801. By specifically inhibiting DNA methyltransferase, the enzyme required for methylation, the aberrant methylation of the tumor suppressor genes can be prevented.

3. Treatment of Different Disease States

Described herein are several different disease states which may be treated by the combination therapy methods and compositions provided herein. It is noted that other disease states that may be treated with imatinib mesylate may also be treated with the combination of imatinib mesylate and a DNA methylation inhibitor where the DNA methylation inhibitor synergistically renders the imatinib mesylate more effective, for example by reducing resistance to imatinib mesylate that the patient may naturally have or may develop over time.

A. Chronic Myelogenous Leukemia

Unlike other forms of leukemia, CML is a homogeneous disease. Almost all patients with CML (90%) have the same chromosomal abnormality in their leukemic cells. In up to 40% of CML patients, the disease progresses directly from the chronic to the blastic phase. Cortes and Kantarjian (1998) in Cancer management: a multidisciplinary approach, 2d ed. Huntington, N.Y.: Publisher Research Management, Inc, p306–15. Blast transformation typically occurs at 3 to 5 years, but onset is random and may be observed at the time of initial diagnosis. Common features for chronic phase CML patients include fatigue, weight loss, and signs or symptoms of splenomegaly (e.g., left upper quadrant pain, abdominal fullness, a palpable mass), which occurs in up to 70% of patients. Cortes et al (1996) Am J Med 100(5):555–70. Patients with extreme elevations in white blood cell count (hyperleukocytosis) may demonstrate signs or symptoms of leukostasis, including mental status changes, focal neurologic deficits, tinnitus, dyspnea, and priapism. Rtinal hemorrhages or other bleeding manifestations may appear irrespective of platelet counts. This is attributable to the qualitative platelet dysfunction that is common in CML. Goldman (1997) BMJ (Clin Res Ed) 314:657–60.

As CML progresses from chronic phase to accelerated phase, the patient may experience fever, night sweats, weight loss, and progressive splenomegaly. More often, however, there is no significant change in symptoms, and onset is heralded by hematologic progression (e.g., worsening of blood counts) or cytogenetic evolution (e.g., development of new chromosomal abnormalities). As CML progresses from the accelerated phase to blast phase, the patient may experience fever, weight loss, night sweats, bone pain, and constitutional symptoms. Lymphadenopathy, leukemia cutis, central nervous system disease, and bleeding secondary to progressive thrombocytopenia also may occur.

Hughes and Goldman (1995) in Hematology: basic principles and practice, 2d ed. New York: Churchill Livingstone, p1142–59.

CML staging involves the use of a system of categorization to describe the seriousness of the CML and attempts to put patients with similar prognosis and treatment in the same staging group. Staging is important in developing CML treatment strategies as it allows doctors to compare the efficacy of different treatments for patients with similar conditions, and aids in the determination of treatment decisions. Staging systems for CML are generally based on clinical features with demonstrated prognostic significance, including age, size of spleen, percentage of circulating and marrow blasts, degree of basophilia, extent of thrombocytosis, and presence of atypical chromosomal abnormalities. Faderl, S., Talpaz, M., Estrov, Z., and Kantarjian, H. M. Chronic myelogenous leukemia: biology and therapy. Ann. Intern. Med., 131: 207–219, 1999; Grier HE, Civin CI. Myeloid Leukemias, Myelodysplasia, and Myeloproliferative Diseases in Children. In (Nathan and Oski, eds) Hematology of Infancy and Childhood, volume 2". $5^{th}$ Edition, W. B. Saunders Company, 1998; 34:1286–1459; Santini, V., Kantarjian, H. M., and Issa, J. P. Changes in DNA methylation in neoplasia: pathophysiology and therapeutic implications. Ann. Intern. Med., 134: 573–586, 2001; Lubbert M, Wijermans P, Kunzman R, et al. Cytogenetic responses in high-risk myelodysplastic syndrome following low-dose treatment with the DNA methylation inhibitor 5-aza-2'-deoxycytidine. Br J Haematol 2001 Aug; 114(2):349–357. In addition, specific response to interferon alpha-2b therapy is considered to be a particularly sensitive predictor of long-term survival following treatment. Goldman (1997) Baillieres Clin Haematol 10(2): 405–21.

Prior to the administration of a DNA methylation inhibitor, CML patients may optionally be staged to determine the severity of the CML. Staging may include determining the number of blasts, promyelocytes, basophil, and platelets per liter of peripheral blood or bone marrow.

Patients with CML in the chronic phase have all of the following conditions: less than 15% blasts in the peripheral blood or bone marrow; less than 30% blasts and promyleocytes in the peripheral blood or bone marrow; less than 20% basophils in the peripheral blood; 100 times 10 supra 9 per liter platelets; and no extramedullary involvement other than liver or spleen. Patients with CML in the accelerated phase have at least one of the following conditions: 15% to less than 30% blasts in the peripheral blood or bone marrow; 30% blasts and promyleocytes in the peripheral blood or bone marrow (but less than 30% blasts in the peripheral blood or bone marrow); 20% basophils in the peripheral blood; or less than 100 times 10 supra 9 per liter platelets.

Blast phase CML patients have at least 30% blasts and promyleocytes in the peripheral blood or bone marrow, or extramedullary involvement other than liver or spleen.

Preferable blast phase CML patients treated using the compositions and methods of the present invention are two years of age or older, have histologically confirmed diagnosis of blast phase CML, were previously treated with imatinib mesylate with no response or resulted in loss of response, and have bilirubin levels greater than or equal to 1.5 times the upper limit of normal, serum glutamic-oxaloacetic transaminase and serum glutamic-pyruvic transaminase levels greater than or equal to 2.5 times the upper limit of normal, and serum creatine levels greater than or equal to 1.5 times the upper limit of normal.

Patients with CML in chronic, accelerated or blast phase, who are resistant to standard therapy generally have a relatively poor prognosis with a rapid progression to blast crisis, bone marrow failure and death. To measure the success of a therapeutic treatment of CML, hematologic responses are determined. A complete hematologic response is defined as maintaining the following conditions for four weeks: less than or equal to 5% blasts in bone marrow; no peripheral blood blasts; absolute neutrophil count of greater than 1.5 times 10 supra 9 per liter; platelet count of greater than 100 times 10 supra 9 per liter; and no extramedullary involvement.

The Philadelphia chromosome, with the Bcr-Abl oncogene detectable at the molecular level, is present at diagnosis in 95% of patients. Optionally, complete hematologic responses are further classified according to suppression of the Philadelphia chromosome (Ph). For example, a patient with complete hematologic response and greater than 65% Ph positive is classified as no cytogenetic response. Patient responses that are 36% to 65% Ph positive are classified as minimal cytogenetic responses, 1% to 35% Ph positive are partial cytogenetic responses, and 0% Ph positive are complete cytogenetic responses.

A partial hematologic response is defined as maintaining the following conditions for four weeks: less than or equal to 5% blasts in bone marrow; no peripheral blood blasts; absolute neutrophil count of less than 1.5 times 10 supra 9 per liter; and platelet count of less than 100 times 10 supra 9 per liter.

A hematologic improvement is defined as maintaining the following conditions for four weeks: less 15% blasts in bone marrow and peripheral blood; less than 40% blasts and promyeloctes in peripheral blood and blood marrow; less than 20% basophils in peripheral blood; and no extramedullary involvement other than liver or spleen.

CML disease progression is associated with hypermethylation of a promoter region within Bcr-Abl. J-P Issa et al (1999) Blood 93:2075–2080. In mammalian cells, approximately 3% to 5% of the cytosine residues in genomic DNA are present as 5-methylcytosine. Ehrlich et al (1982) Nucleic Acid Res. 10:2709–2721. This modification of cytosine takes place after DNA replication and is catalyzed by DNA methyltransferase using S-adenosyl-methionine as the methyl donor. Approximately 70% to 80% of 5-methylcytosine residues are found in the CpG sequence. Bird (1986) Nature 321:209–213. This sequence, when found at a high frequency, in the genome, is referred to as CpG islands. Unmethylated CpG islands are associated with housekeeping genes, while the islands of many tissue-specific genes are methylated, except in the tissue where they are expressed. Yevin and Razin (1993) in DNA Methylation: Molecular Biology and Biological Significance. Basel: Birkhauser Verlag, p523–568. This methylation of DNA has been proposed to play an important role in the control of expression of different genes in eukaryotic cells during embryonic development. Consistent with this hypothesis, inhibition of DNA methylation has been found to induce differentiation in mammalian cells. Jones and Taylor (1980) Cell 20:85–93.

Methylation of DNA in the regulatory region of a gene can inhibit transcription of the gene. This may be because 5-methylcytosine protrudes into the major groove of the DNA helix, which interferes with the binding of transcription factors.

The methylated cytosine in DNA, 5-methylcytosine, can undergo spontaneous deamination to form thymine at a rate much higher than the deamination of cytosine to uracil. Shen et al. (1994) Nucleic Acid Res. 22:972–976. If the deamination of 5-methylcytosine is unrepaired, it will result in a C to T transition mutation. For example, many "hot spots" of DNA damages in the human p53 gene are associated with CpG to TpG transition mutations. Denissenko et al. (1997) Proc. Natl. Acad. Sci. USA 94:3893–1898.

B. Treatment of Chronic Myelogenous Leukemia

In a particular embodiment, a method is provided for treating CML. It has been found that unchecked production of tyrosine kinase Bcr-Abl leads to excessive levels of white blood cells in the blood and bone marrow, but disrupts the normal production of white blood cells; and imatinib mesylate works specifically to block the activity of Bcr-Abl tyrosine kinase. However, methylation of Bcr-Abl has been found to correlate with progression with CML: hypermethylation in 24–68% of CML patients in the chronic phase, while patients in the accelerated phase and blast crisis had hypermethylation frequencies at 73% and 80%, respectively. Issa et al. (1999) Blood 93:2075–2080.

Other than Bcr-Abl gene, multiple genes, including the p15/Ink-4b cell-cycle regulator gene, are found to contain aberrant methylation in more advanced stages of CML. Cortes et al (1997) Baillieres Clin Haematol 10(2):277–90. Aberrations in DNA methylation, whether general or site specific, are common in cancer and have important roles in tumor initiation, progression and resistance. Lubbert et al (2001) Br J Haematol 114(2):349–357. Methylation of the p15 promoters is associated with progression of CML. Nguyen et al. (2000) Blood 95:2990–2992.

The inventors believe that hypermethylation of p 15 would lead to loss of its tumor suppression function and accelerates transformation induced by Bcr-Abl, ultimately leading to resistance to the treatment of CML with imatinib mesylate. Administering a DNA methylation inhibitor to a CML patient may re-establish the tumor suppression functions of p 15, which, in turn, leads to sensitization of the patient to the treatment with imatinib mesylate or results in patient response to disease.

The present invention provides a method of treating a patient having chronic myelogenous leukemia, comprising: administering to a patient having chronic myelogenous leukemia but resistant to the treatment with imatinib mesylate a therapeutically effective amount of a DNA methylation inhibitor. In one variation, the patient has already manifested resistance to imatinib mesylate within 6 months of the treatment with imatinib mesylate as defined by no improvement in the prognosis or worsening of the prognosis.

The DNA methylation inhibitor may be optionally administered to the patient in the blast, chronic or accelerated phase of chronic myelogenous leukemia. In one embodiment of the present invention, a method is provided for treating patients having blast phase CML, where prior to treatment, the patient's CML is staged. The method comprises administering to a patient suffering from blast phase CML, after the CML has been staged, a DNA methylation inhibitor. Optionally, staging the CML includes determining the number of blasts, promyelocytes, basophil, and platelets per liter of peripheral blood or bone marrow. Optionally, the patient in blast phase of CML has more than 30% blasts in the peripheral blood or bone marrow.

A method is also provided for treating a patient having chronic myelogenous leukemia but manifesting intolerance to imatinib mesylate. The method comprises: administering to the patient a therapeutically effective amount of a DNA methylation inhibitor which mitigates the imatinib mesylate intolerance.

Preferably, the DNA methylation inhibitor is administered to a patient who has already manifested intolerance to imatinib mesylate within 6 months of the treatment with imatinib mesylate. The patient's intolerance to imatinib mesylate can be defined by manifesting symptoms or adverse effects such hepatoxicity, fluid retention syndrome, neutropenia, hemorrhage, dyspepsia, dyspnea, diarrhea, muscle cramps, skin rash, fatigue, headache, nausea, vomiting, and thrombocytopenia.

A method is also provided for treating a patient having chronic myelogenous leukemia, comprising: co-administering to the patient imatinib mesylate and decitabine such that the patient's resistance to imatinib mesylate in the absence of decitabine is reduced.

In one variation, imatinib mesylate is administered to the patient at a dose of 100–800 mg/day. For chronic phase CML patients, imatinib mesylate is preferentially administered at a dose of 200–400 mg/day. For accelerated or blast phase CML patients, imatinib mesylate is preferably administered at a dose of 500–800 mg/day.

In another embodiment of the present invention, a composition is provided that comprises a DNA methylation inhibitor and imatinib mesylate. The DNA methylation inhibitor may optionally be a cytidine analog such as cytosine arabinoside. In one variation, the cytidine analog is decitabine. In one variation, the composition is formulated for intravenous or subcutaneous administration. The inventive combination of DNA methylation inhibitor and imatinib mesylate may be administered by a variety of routes, and may be administered or co-administered in any conventional dosage form. Co-administration in the context of this invention is defined to mean the administration of more than one therapeutic in the course of a coordinated treatment to achieve an improved clinical outcome. Such co-administration may also be coextensive, that is, occurring during overlapping periods of time. For example, the DNA methylation inhibitor may be administered to a patient before, concomitantly, or after imatinib mesylate is administered. In one variation, the patient is treated first with imatinib mesylate and then treated with the DNA methylation inhibitor (e.g., decitabine). The following is a brief description of how decitabine may be administered to a CML patient in a clinic setting.

Patients with CML receive decitabine at 15 mg/m2 IV over one hour on five consecutive days each week (e.g., Monday through Friday) for two weeks, followed by four weeks rest. For patients who achieve and remain in remission, the treatment continues so long as no adverse drug experiences occur and there is no evidence of disease progression or relapse.

Since the effect of decitabine may be delayed for up to two cycles, patients with high white blood cell counts ($>10\times10^9$ per liter) at study entry optionally receive hydroxyurea (HU) 1–3 g orally daily concomitantly with the first two cycles of decitabine only. The treatment with HU continues until the end of dosing in the second cycle of decitabine (e.g., the 13th day of the second cycle) or until the white blood cell count falls below $10\times10^9$ per liter during the second cycle. This is done to minimize the risks of complications due to hyperleukocytosis while awaiting a response. In general, HU can be given a 1 g daily if the white blood cell count is between $10-40\times10^9$ per liter, 2 g daily if the white blood cell count is $40-50\times10^9$ per liter, and 3 g daily if the white blood cell count is above $50\times10^9$ per liter. Other dose schedules can be used as indicated. Children with white blood cell counts above $10-20\times10^9$ per liter can be treated with HU at 10–20 mg/kg/day. The use of anagrelide is allowed for platelets $>600\times10^9$ per liter, but is generally discontinued prior to decitabine dosing in the third cycle.

Patients achieving an unconfirmed complete or partial hematological response, or a hematologic improvement, will continue to receive therapy every six weeks until they show evidence of disease progression or relapse.

The second and subsequent cycles of decitabine will be instituted when patients have recovered from hematologic or non-hematological toxicity. Hematologic recovery is generally an absolute neutrophil count >1×10$^9$ per liter or to baseline and platelets to >150×10$^9$ per liter, untransfused for the preceding week.

The decitabine dose may be escalated incrementally by 25% to reduce the absolute neutrophil count to between 1×10$^9$ per liter and 1.5×10$^9$ per liter and a platelet count to between 50×10$^9$ per liter and 100×10$^9$ per liter with each cycle. The decitabine dose may be decreased incrementally by 25% in the face of grade 4 hematologic toxicity or grade 3 or 4 non-hematological toxicity, other than alopecia.

C. Other Disease States

Compositions and methods of the present invention may also be used for treating a patient with diseases other than CML, especially diseases associated with activity of protein kinase, and more particularly protein tyrosine kinase.

I. Tyrosine Kinases and Diseases Associated with Their Activities

Enzymes that carry out specific transfer of the γ phosphate of ATP to the hydroxyl group of a tyrosine in a protein substrate are called protein tyrosine kinases (TK). Arteaga C L et al., Overview of rationale and clinical trials with signal transduction inhibitors in lung cancer. Semin Oncol 2002; 29(1 Suppl 4): 15–26. Phosphorylation of Tyr residues modulates enzymatic activity and creates binding sites for the recruitment of a wide variety of downstream signaling proteins. TK play a major role in signal transduction pathways that lead to both the immediate (adhesion, migration, cytoskeletal rearrangements) and the delayed cell responses (i.e., specific protein expression, proliferation) to a variety of extracellular stimuli. The large number of oncogenic protein tyrosine kinases plus the rare presence of phosphotyrosine in nontransformed cells argue persuasively that tyrosine phosphorylation and activation of signaling molecules downstream from receptor tyrosine kinases facilitate growth control and transformation of cells towards malignancy.

TK fall into two large subgroups: the transmembrane receptor TK (RTK) and the nonreceptor TK (NRTK). Zwick E, Receptor tyrosine kinases as targets for anticancer drugs, Trends Mol Med 2002 Janurary;8(1): 17–23. Both groups can be subdivided according to their intracellular regulation, localization and association with different signaling mechanisms.

i) Receptor Tyrosine Kinases and Diseases Associated with Their Activity

Receptor tyrosine kinases are glycoproteins that are activated by binding of their cognate ligands to the extracellular region. Lowes V L, et al., Integration of signals from receptor tyrosine kinases and G protein-coupled receptors, Neurosignals 2002 Janurary-Feburary;11(1):5–19. Ligand binding stabilizes a dimeric configuration of the extracellular domains that is required for a subsequent transduction of the extracellular signal to the cytoplasm. This is achieved by phosphorylation of tyrosine residues on the cytoplasmic portion of the receptors themselves (trans-autophosphorylation) and on downstream signaling proteins. Downregulation of RTK occurs via receptor-mediated endocytosis, ubiquitin-directed proteolysis and dephosphorylation by protein tyrosine phosphatases.

The RTK subgroup comprises families of receptors for the epidermal growth factor (EGFR), vascular endothelial growth factor (VEGFR), nerve growth factor (NGFR), fibroblast growth factor (FGFR), platelet-derived growth factor (PDGFR), insulin and ephrin receptor families, Met and Ror families. Lowes V L, et al., Integration of signals from receptor tyrosine kinases and G protein-coupled receptors, Neurosignals 2002 Janurary-Feburary; 11(1):5–19. Each family may comprise one or more family member that possesses characteristic structural and/or functional similarities. It is also noted that any therapeutic combination for treating malignancies that comprises the DNA methylation inhibitor and an agent inhibiting one or more members belonging to RTK subgroup is falling within the scope of this invention. A chimeric protein comprising a functional unit that is structurally or functionally similar to RTK is considered to belong to RTK subgroup for the purposes of covering the scope of this invention.

a) HER/erbB Family (EGFR Family)

The epidermal growth factor receptor (EGFR, HER1, erbB-1) was the first discovered member of the HER/erbB family of transmembrane receptor tyrosine kinases, which also comprises HER2/neu (erbB-2) and the heregulin/neuregulin receptors HER3 (erbB-3) and HER4 (erbB-4). Filardo E J, Epidermal growth factor receptor (EGFR) transactivation by estrogen via the G-protein-coupled receptor, GPR30: a novel signaling pathway with potential significance for breast cancer, J Steroid Biochem Mol Biol 2002;80(2):231–8. Each ectodomain of EGFR, HER3, and HER4 interacts with a set of soluble ligands, whereas no ligand has been identified for the orphan HER2 receptor. Arteaga C L, et al., Overview of rationale and clinical trials with signal transduction inhibitors in lung cancer. Semin Oncol 2002; 29(1 Suppl 4): 15–26. Binding of ligands to the ectodomain of EGFR, HER3, and HER4 results in the formation of homodimeric and heterodimeric complexes, activation of the intracellular tyrosine kinase activity, and receptor autophosphorylation in specific C-terminal tyrosines, which in turn recruit SH2-containing adaptors and/or second messengers. The signaling pathways that are activated after the initial activation of HER receptors mediate the effects of the receptors on cell proliferation, development, differentiation, migration, and oncogenesis, and include the p42 and p44 mitogen-activated protein kinases, phosphatidylinositol 3-kinase (PI3K), the stress-activated protein kinases, phospholipase C, Src, and the family of signal transducers and activator of transcription. Lohrisch C, et al., HER2/neu as a predictive factor in breast cancer, Clin Breast Cancer 2001 2(2): 129–35.

Several epithelial tumors, particularly carcinomas of the upper aerodigestive tract, including lung cancer and non-small cell lung cancer (NSCLC), display overexpression with or without gene amplification of EGFR family member. The EGFR family member(s) is overexpressed in a majority of human carcinomas as compared with their nontransformed counterpart. Meric F, et al., HER2/neu in the management of invasive breast cancer, J Am Coll Surg 2002, 194(4): 488–501.

The homology among HER receptors like EGFR and HER2 facilitates generation of bifunctional inhibitors such as PD168393, CI1033, and EKB-569. Optionally, chemical modification may be made to generate irreversible inhibitors that bind covalently to specific Cys residues in the EGFR ATP-binding pocket, thus creating irreversible inhibitors such as CI1033 and EKB-569. Low molecular weight of the inhibitors may allow them to penetrate tumor sites better, but also makes them much less stable in vivo than antireceptor antibodies. They can be administered orally, which makes them highly suitable for chronic therapy. In addition, the irreversible inhibitors, such as irreversible inhibitors that bind covalently to specific Cys residues in the EGFR ATP-binding pocket, like CI1033 and EKB-569, may achieve a longer in situ half-life at its molecular target site relative to that of reversible EGFR, possibly leading to improved efficacy of the therapy, but also increasing the overall possible toxicity. CI-1033, a erbB tyrosine kinase inhibitor, is a clinically promising agent that is active against all four members of the erbB receptor tyrosine kinase family. In vitro studies of human cancer cell lines indicate that CI-1033 results in prompt, potent, and sustained inhibition of tyrosine kinase activity. This inhibition is highly selective for erbB I (epidermal growth factor receptor), erbB2, erbB3, and erbB4 without inhibiting tyrosine kinase activity of receptors such as platelet-derived growth factor receptor, fibroblast growth factor receptor, and insulin receptor, even at high concentrations. Slichenmyer W J, et al., CI-1033, a pan-erbB tyrosine kinase inhibitor, Semin Oncol 2001 October; 28(5 Suppl 16):80–5. Another example of a potent HER inhibitor is a monoclonal antibody Trastuzumab (Herceptin®). Currently, herceptin is applied in HER2 associated breast cancer treatment and in clinical trail designated to treat HER2 associated malignances of various types (clinical trails held by Cancer Hospital—Ohio State University, Ohio).

Other than Herceptin®, examples of the inhibitors of epidermal growth factor receptor family include, but are not limited to, ZD1839 (Iressa®), PD168393, CI1033, IMC-C225, EKB-569, and inhibitors binding covalently to Cys residues of the EGF receptor tyrosine kinase.

ZD1839 has been shown to be a selective EGF receptor-tyrosine kinase inhibitor which can be orally administered to patients with solid malignant tumors. Ranson M, et al. J Clin Oncol 2002 May 1 ;20(9):2240–50. IMC-C225 is a chimeric monoclonal antibody that targets extracellular epidermal growth factor receptor; it has shown both in vitro and in vivo antitumor activity in tumor cells lines expressing epidermal growth factor receptor, including heightened radiation response in vitro in cultured human squamous cell carcinoma and enhancement of taxane- and platinum-induced cytotoxicity in non-small cell lung cancer xenografts. Herbst R S and Langer C J, Semin Oncol 2002 29 (1 Suppl 4):27–36.

Co-administration of DNA-methylation inhibitor in conjunction with one or more inhibitor(s) of member(s) of this family may be specifically advantageous in treatment of human carcinomas.

b) PDGFR Family

The compositions and methods of the present invention may be used to treat diseases associated with tyrosine kinase activity of platelet-derived growth factor (PDGF) receptor such as prostate cancer and glioblastoma. PDGF, such as PDGF A and B, signals through a cell surface tyrosine kinase receptor (PDGF-R) to stimulate various cellular functions including growth, proliferation, and differentiation. George (2001) Semin. Oncol. 28 (5 Suppl 17): 27–33. PDGF expression has been shown in various different types of solid tumors, such as prostate cancer and glioblastoma. Both PDGF-R and Bcr-Abl signal through the Ras/MAP kinase pathway.

The inventors believe that by inhibiting the activity of PDGF-R and DNA methylation using the composition and methods of the present invention, diseases associated with tyrosine kinase activity of PDGF-R can be treated more efficaciously and with significantly reduced adverse effects.

c) VEGFR Family

Vascular endothelial growth factor (VEGF) is a potent and specific angiogenic factor Verheul H M at al., The Role of Vascular Endothelial Growth Factor (VEGF) in Tumor Angiogenesis and Early Clinical Development of VEGF-Receptor Kinase Inhibitors. Clin Breast Cancer 2000 1 : S80–4. Originally identified for its ability to induce vascular permeability and stimulate endothelial cell growth, VEGF is now known to facilitate tumor growth. The family of VEGF receptors comprises high-affinity tyrosine kinase receptors VEGFR1, VEGFR2, and VEGFR3, of which VEGFR-Flk-1/KDR (VEGFR-2) is exclusively expressed in vascular endothelial cells.

These receptors are believed to play a role in angiogenesis, the formation of new blood vessels from preexisting vasculature that is crucial for solid tumor growth and metastasis formation. Inhibition of tumor angiogenesis may be a promising therapeutic strategy to combat solid tumors. The clinical importance of VEGFR family member (s) for tumor growth is supported by the fact that most tumors produce VEGF and that the inhibition of VEGF-induced angiogenesis significantly inhibits tumor growth in vivo. Because the VEGFR-2 system is a dominant signal-transduction pathway in regulating tumor angiogenesis, specific inhibitors of this pathway inhibit metastases, microvessel formation, and tumor-cell proliferation. Induction of apoptosis in tumor cells and endothelial cells has also been observed. Verheul H M at al., The Role of Vascular Endothelial Growth Factor (VEGF) in Tumor Angiogenesis and Early Clinical Development of VEGF-Receptor Kinase Inhibitors. Clin Breast Cancer 2000 1 :S80–4.

SU6668 is a small molecule inhibitor of the angiogenic receptor tyrosine kinases Flk-1/KDR, PDGFRbeta, and FGFR1. SU6668 treatment induced apoptosis in tumor microvessels within 6 h of the initiation of treatment. Dose-dependent decreases in tumor microvessel density were observed within 3 days of the first treatment. These changes were accompanied by decreased tumor cell proliferation and increased tumor cell apoptosis. In summary, SU6668-induced inhibition of angiogenic receptor tyrosine kinase activity in vivo is associated with rapid vessel killing in tumors, leading to broad and potent antitumor effects. Laird A D, et al., SU6668 inhibits Flk-1/KDR and PDGFR-beta in vivo, resulting in rapid apoptosis of tumor vasculature and tumor regression in mice, FASEB J 2002; 16(7) :681–90.

Co-administration of DNA-methylation inhibitor in conjunction with one or more inhibitor(s) of member(s) of this family may be specifically advantageous in treatment of solid and/or metastasis-prone tumors.

d) NGFR Family

Neurotrophins are target-derived soluble factors required for neuronal survival. Nerve growth factor (NGF) the founding member of the neurotrophin family, binds to two types of receptors: Trk tyrosine kinase and the p75 neurotrophin receptor, which belongs to the Fas-tumor necrosis factor (TNF) receptor superfamily. Casaccia-Bonnefil P, et al., Neurotrophins in cell survival/death decisions, Adv Exp Med Biol 1999; 468:275–82. Binding of neurotrophins to Trk receptor tyrosine kinases initiate signaling cascades that promote cell survival sand differentiation. In contrast, p75 NGFR has been shown to modulate the susceptibility to death of selective cellular populations—including differentiated rat oligodendrocytes—in specific conditions. Trk mediated signals spatiotemporally regulate neural development and maintenance of neural network. Nakagawara A, Trk receptor tyrosine kinases: a bridge between cancer and neural development, Cancer Lett 2001 Aug 28; 169(2): 107–14. Further examples of trk family include, but are not limited to trkB and trkC. These genes are highly related to the trk proto-oncogene and encode tyrosine protein kinases which serve as functional receptors for the NGF-related neurotrophins brain-derived neurotrophic factor (BDNF) and neurotrophic-3 (NT-3), respectively. Lamballe F, et al., The trk family of oncogenes and neurotrophin receptors, Princess Takamatsu Symp 1991; 22:153–70.

Trk may be observed as a rearranged oncogene fused with the tropomyosin gene in the extracellular domain in non-neuronal neoplasms such as colon and papillary thyroid cancers. This oncogene encodes a chimeric molecule that contains the 221 amino terminal residues of a non-muscle tropomyosin followed by the transmembrane and cytoplasmic domains of the trk proto-oncogene product, a tyrosine protein kinase receptor. trk oncogenes have also been identified in a significant fraction of thyroid papillary carcinomas. Some of these trk oncogenes contain sequences derived from genes other than tropomyosin. The signals through the receptors encoded by Trk member may regulate growth, differentiation and apoptosis of the tumors with neuronal origin such as neuroblastoma and medulloblastoma. Barbacid M, et al., The trk family of tyrosine protein kinase receptors, Biochim Biophys Acta 1991 Dec. 10; 1072(2–3): 115–27.

The indocarbazole compounds, CEP-701 and CEP-75 1, are potent inhibitor of this Trk receptor survival signaling. These inhibitors selectively induce apoptosis of prostate cancer cells and osteoblasts in various in vitro and in vivo models. Pinski J et. Al., Trk receptor inhibition induces apoptosis of proliferating but not quiescent human osteoblasts, Cancer Res 2002 Feb. 15; 62(4):986–9.

Co-administration of DNA-methylation inhibitor in conjunction with one or more inhibitor(s) of member(s) of this family may be specifically advantageous in treatment of tumors of mesodermal origin, including but not limited to prostate, colon, papillary and thyroid cancers, neuromas and osteoblastomas.

e) Met Family

The Met family comprises transmembrane proteins belonging to the subgroup of receptor tyrosine kinases. Danilkovitch-Miagkova, A. et al., Dysregulation of Met receptor tyrosine kinase activity in invasive tumors, J Clin Invest, 2002, 109, 863–867. Typically, a member of this family is synthesized as a single-chain precursor, which undergoes intracellular proteolytic cleavage at a basic amino acid site, yielding a disulfide-linked heterodimer. Its C-terminal, intracellular region contains a multifunctional docking site that binds to various signaling molecules. The Met receptor tyrosine kinase family comprises related proteins, Met, Ron, and c-Sea. Cooper, C. S. et al.1984. Molecular cloning of a new transforming gene from a chemically transformed human cell line. Nature. 311:29–33. Ron shares many common structural features, and signaling pathways with Met. For example, activated Ron may transphosphorylate Met, and vice versa. Pre-existing, ligand-independent heterodimers between Met and Ron have been detected on the cell surface, indicating that these receptors are colocalized and may be able to transphosphorylate and to activate one another. Danilkovitch-Miagkova, A. et al., Dysregulation of Met receptor tyrosine kinase activity in invasive tumors, J Clin Invest, 2002, 109, 863–867, Forrester W C, The Ror receptor tyrosine kinase family, Cell Mol Life Sci 2002; 59 (1): 83–96.

The ligand of the Met receptor is hepatocyte growth factor (HGF), also known as scatter factor. Bottaro, D. P. et al., 1991. Identification of the hepatocyte growth factor receptor as the c-met proto-oncogene product. Science. 251:802–804. HGF is a multifunctional factor affecting a number of cell targets including epithelium, endothelium, myoblasts, spinal motor neurons, and hematopoietic cells. Signaling pathways activated by the HGF-Met interaction mediate cell adhesion and motility. These pathways, coupled to tightly regulated changes in cell growth, morphology, and survival, define a general pattern of invasive growth of tumorogenic tissues. Comoglio, P. M., and Trusolino, L. 2002. Invasive growth: from development to metastasis. J. Clin. Invest. 109:857–862.

Met is involved in malignant cell transformation. Dysregulation of Met activity in cells plays a particular role in tumor invasive growth, a stage of tumor progression leading to metastases, so that overexpression and hyperactivation of Met correlate with metastatic ability of the tumor cells. One oncogenic form of Met is a product of the TPR-MET fusion, which arises through a chromosomal rearrangement. Increased Met expression has been found in papillary carcinomas of the thyroid gland, in carcinomas of colon, pancreas, and ovary, in osteogenic sarcomas, and in other types of cancer. Point mutations in MET have been identified in hereditary and sporadic papillary renal carcinomas hepatocellular and gastric carcinomas, and head and neck squamous carcinomas. Danilkovitch-Miagkova, A. et al., Dysregulation of Met receptor tyrosine kinase activity in invasive tumors, J Clin Invest, 2002, 109, 863–867.

Co-administration of DNA-methylation inhibitor in conjunction with one or more inhibitor(s) of member(s) of this family and/or their ligands may be specifically advantageous in treatment of tumors that are characterized by invasive in-growth.

f) Ror Family

Ror RTKs are a family of orphan receptors that are related to muscle specific kinase (MuSK) and Trk neurotrophin receptors. MuSK assembles acetylcholine receptors at the neuromuscular junction, and Trk receptors function in the developing nervous system. Forrester W C, The Ror receptor tyrosine kinase family, Cell Mol Life Sci 2002 Janurary; 59(1):83–96.

Co-administration of DNA-methylation inhibitor in conjunction with one or more inhibitor(s) of member(s) of this family may be specifically advantageous in treatment of tumors of neurological and/or muscular origins.

ii) Non-Receptor Tyrosine Kinases and Diseases Associated with Their Activity

Non-receptor tyrosine kinases are mostly integral components of the signaling cascades triggered by RTK and by other cell surface receptors such as G protein-coupled receptors and receptors of the immune system. NRTK lack the extracellular ligand-binding domain and a transmembrane-spanning region. With a few exceptions, NRTK are activated by phosphorylation of tyrosines in the activation loop. This is achieved via trans-autophosphorylation or phosphorylation by a different NRTK. In some cases, phosphorylation at Tyr outside of the activation loop negatively regulates the NRTK activity. NRTK are downregulated by dephosphorylation with protein tyrosine phosphatases.

The NRTK subgroup comprises c-kit, Src, Fes, JAK, Fak, Btk, Syk/ZAP-70, and Abl families. Sada K., et al., Structure and function of Syk protein-tyrosine kinase, J Biochem (Tokyo) 2001 August; 130(2):177–86. Each family may comprise one or more family member that possesses characteristic structural and/or functional similarities. It is also noted that any therapeutic combination for treating malignancies that comprises the DNA methylation inhibitor and an agent inhibiting one or more members belonging to RTK subgroup is falling within the scope of this invention. A chimeric protein comprising a functional unit that is structurally or functionally similar to NRTK is considered to belong to NRTK subgroup for the purposes of covering the scope of this invention.

Most NRTKs are localized in cytoplasm (Src family, Jak/Tyk family, Zap70/Syk, Lck, Fyn), while some are localized in nucleus (Abl, Fer, Fgr) or could be anchored to the cell membrane through the N-terminal modification, such as meristoylation and palmitoylation. Sada K., et al., Structure and function of Syk protein-tyrosine kinase, J Biochem (Tokyo) 2001 August; 130(2):177–86. The focal adhesion kinase (Fak) is the only member of NRTK that is an integrin-binding and may be activated by the overall structure of the focal adhesion junction, rather than by a single activated receptor. In addition to the kinase domain, NRTK feature domains that mediate protein-protein, protein-lipid, and protein-DNA interactions. The most common are the Src homology 2 (SH2) and 3 (SH3) domains that bind, respectively, phosphotyrosine residues in a sequence-specific manner and proline-containing sequences capable of forming a polyproline type II helix. Some NRTK lack SH2 and SH3 domains but contain subfamily-specific domains used for other interactions, such as Jak homology domains for targeting to cytoplasmic region of cytokine receptors (Jak), integrin- and focal adhesion binding domains (Fak), DNA-binding and F-actin-binding domains (Abl). The Btk/Tec subfamily of NRTK has another modular, pleckstrin homology (PH) domains that bind to phosphatidylinositol molecules that have been phosphorylated at particular positions. Thus, different signaling molecules can be selectively recruited by NRTK through their distinct modular domains to RTK activated by extracellular stimuli; NRTK thereby provide a specific routing of extracellular signals to certain intracellular targets.

a) C-Kit Family

The compositions and methods of the present invention may also be used to treat diseases associated with tyrosine kinase activity of the transmembrane protein c-Kit such as gastrointestinal stromal tumor (GIST) and small cell lung cancer (SCLC). c-Kit is defined by the CD117 antigen and is the product of the c-kit proto-oncogene. Activating or gain-of-function mutations in the c-kit gene have been identified in the majority of GISTs. As a result, Kit is constitutively expressed to provide growth and survival signals to GIST cells, which are crucial to the pathogenesis of the disease. So far, GIST has been found to be the most common mesenchymal tumor of the GI tract and resistant to chemotherapy and radiation treatment. Recently, the US Food and Drug Administration (FDA) has approved imatinib mesylate (or GLEEVAC®) for the treatment of patient with KIT (or CD117)-positive unresectable and/or metastatic malignant GISTs.

The inventors believe that while imatinib mesylate can suppress GIST growth by inhibiting the tyrosine kinase activity of c-Kit, mutations in c-kit may render the disease less responsive to the treatment with imatinib mesylate. In addition, hypermethylation in the genes participating in the signal transduction pathway of c-Kit would also lead to transformation of c-Kit, ultimately leading to resistance to imatinib mesylate treatment. By targeting c-Kit and DNA hypermethylation using the combination therapy of the present invention, diseases associated with tyrosine kinase activity of c-Kit can be treated more efficaciously and with significantly reduced adverse effects.

b) Src Family

Src tyrosine kinases are signal transducers that modulate a wide variety of cellular functions. Ma Y C, et al., Novel regulation and function of Src tyrosine kinase, Cell Mol Life Sci 2002, 59(3): 456–62. Misregulation of Src leads to cell transformation and cancer. Src homology 2 (SH2) domains are found in many intercellular signal-transduction proteins which bind phosphotyrosine containing polypeptide sequences with high affinity and specificity and are considered potential targets for drug discovery. Src is normally maintained in an inactive state, but can be activated transiently during cellular events such as mitosis, or constitutively by abnormal events such as mutation (i.e. v-Src and some human cancers). Activation of Src occurs as a result of disruption of the negative regulatory processes that normally suppress Src activity, and understanding the various mechanisms behind Src activation has been a target of intense study. Src associates with cellular membranes, in particular the plasma membrane, and endosomal membranes. Studies indicate that the different subcellular localizations of Src could be important for the regulation of specific cellular processes such as mitogenesis, cytoskeletal organization, and/or membrane trafficking. Bjorge J D, et al., Selected glimpses into the activation and function of Src kinase, Oncogene 2000 Nov. 20; 19(49): 5620–35.

The examples of members of Src family include, but are not limited to Src, c-Src, v-Src, Yes, c-Yes, v-Yes, Fyn, Lyn, Lck, Blk, Hek, Fgr, c-Fgr, v-Fgr, p56lck, Tkl, Csk, Ctk and their homologs. It is noted that these examples are present here for illustrative, rather then limiting purposes, so that other peptides that share structural and/or functional similarities with the members of Src family are fall within the scope of this invention.

The examples of Src inhibitors include, but are not limited to SU 101 and CGP 57418B. Broadbridge R J, et al., The Src homology-2 domains (SH2 domains) of the protein tyrosine kinase p56lck: structure, mechanism and drug design, Curr Drug Targets 2000 December; 1(4):365–86.

The examples of diseases associated with abnormal activity of Src tyrosine kinases include, but are not limited to breast cancer, carcinoma, such as colorectal carcinoma, myeloma, leukemia, and neuroblastoma. Co-administration of DNA-methylation inhibitor in conjunction with one or more inhibitor(s) of member(s) of this family may be specifically advantageous in treatment of breast cancer, carcinoma, myeloma, leukemia, and neuroblastoma.

c) Fes Family

Fes is a tyrosine kinase that contains SH2 domain, but no SH3 domain or carboxy terminal regulatory phosphotyrosine such as found in the Src family of kinases. Fes has a unique N-terminal domain of over 400 amino acids of unknown function. It has been implicated in signaling by a variety of hematopoietic growth factors, and is predominantly a nuclear protein. Although originally identified as a cellular homolog of several transforming retroviral oncoproteins, Fes was later found to exhibit strong expression in myeloid hematopoietic cells and to play a direct role in their differentiation. Yates K E, Role of c-Fes in normal and neoplastic hematopoiesis, Stem Cells 1996 Janurary; 14(1):117–23.

The members of Fes family include, but are not limited to c-fes/fps, v-fps/fes, p94-c-fes-related protein, Fer, Fes-homologs, and Fer-homologs. It is noted that these examples are present here for illustrative, rather then limiting purposes, so that other peptides that share structural and/or functional similarities with the members of Fes family are fall within the scope of this invention.

The examples of diseases associated with abnormal activity of members of Fes family of tyrosine kinases include, but are not limited to carcinoma, neuroblastoma, and tumors of hematopoietic origin. Co-administration of DNA-methylation inhibitor in conjunction with one or more inhibitor(s) of member(s) of this family may be specifically advantageous in treatment of tumors of mesenchymal and hematopoietic origin.

d) JAK Family

The Janus kinase (JAK) family is one of intracellular protein tyrosine kinases (PTKs) present in hematopoietic and lymphoid cells and has been shown to play a crucial role in a variety of biological responses. JAK kinase function may integrate components of diverse signaling cascades. JAK kinase function is required for optimal activation of the Src-kinase cascade, the Ras-MAP kinase pathway, the PI3K-AKT pathway and STAT signaling following the interaction of cytokine/interferon receptors with their ligands. For example, Jak-STAT signaling pathway is broadly used by interferons and type I cytokines. Leonard W J. Role of Jak kinases and STATs in cytokine signal transduction. Int J Hematol 2001 April; 73(3):271–7.

The examples of members of JAK family include, but are not limited to Jak1, Jak2, Tyk2, Jak3 and their homologs. It is noted that these examples are present here for illustrative, rather then limiting purposes, so that other peptides that share structural and/or functional similarities with the members of JAK family are fall within the scope of this invention.

The examples of Jak inhibitors include, but not limited to tyrphostins and CIS/SOCS/Jab family. Aringer M, et al., Janus kinases and their role in growth and disease. Life Sci 1999; 64(24):2173–86. For example, the activity of JAK2 may be inhibited by a synthetic component AG490. Miyamoto N, et al., The JAK2 inhibitor AG490 predominantly abrogates the growth of human B-precursor leukemic cells with 11 q23 translocation or Philadelphia chromosome. Leukemia 2001; 15(11):1758–68. The examples of JAK3 inhibitors include, but are not limited to dimethoxyquinazoline compounds, such as 4-(phenyl)-amino-6,7-dimethoxyquinazoline (parent compound WHI-258), the derivatives of this compound that contain an OH group at the 4' position of the phenyl ring, WHI-P131 [4-(4'-hydroxyphenyl)-amino-6,7-dimethoxyquinazoline], WHI-P 154 [4-(3'-bromo-4'-hydroxylphenyl)-amino-6,7-dimethoxyquinazoline], and WHI-P97 [4-(3',5'-dibromo-4'-hydroxylphenyl)-amino-6,7-dimethoxyquinazolin e]. These compounds inhibited JAK3 in immune complex kinase assays in a dose-dependent fashion. Sudbeck E A, et al., Structure-based design of specific inhibitors of Janus kinase 3 as apoptosis-inducing antileukemic agents. Clin Cancer Res 1999 June; 5(6): 1569–82.

Over-activation of JAK kinases has been implicated in tumorigenesis, particularly in progression of leukemia. In contrast, loss of JAK kinase function has been found to result in disease states such as severe-combined immunodeficiency. Aringer M, et al., Janus kinases and their role in growth and disease. Life Sci 1999; 64(24): 2173–86. Co-administration of DNA-methylation inhibitor in conjunction with one or more inhibitor(s) of member(s) of this family may be specifically advantageous in treatment of tumors of mesenchymal, neurological, and hematopoietic origin.

e) Fak Family

Focal adhesion kinase (FAK) is a tyrosine kinase ubiquitously expressed in cells. FAK associates with several different signaling proteins such as Src-family PTKs, p130Cas, Shc, Grb2, PI 3-kinase, and paxillin. This enables FAK to function within a network of integrin-stimulated signaling pathways leading to the activation of targets such as the ERK and JNK/mitogen-activated protein kinase pathways. Fak autophosphorylation is followed by a submembranous localization that facilitates cell spreading, cell migration, cell proliferation, and prevention of apoptosis. Schlaepfer D D, et. el., Signaling through focal adhesion kinase, Prog Biophys Mol Biol 1999;71(3–4):435–78.

The examples of members of Fak family include, but are not limited to Fak, CAKβ/Pyk2/RAFTK and their homologs. It is noted that these examples are present here for illustrative, rather then limiting purposes, so that other peptides that share structural and/or functional similarities with the members of Fak family are fall within the scope of this invention.

The examples of FAK inhibitors include, but are not limited to a dominant negative mutant, S1034-FRNK; a metabolite from Isaria sinclarii, FTY720, that is an antitumor agent for an androgen-independent prostate cancer cell; and FAK antisense oligonucleotide, ISIS 15421. Hauck C R, et al., Inhibition of focal adhesion kinase expression or activity disrupts epidermal growth factor-stimulated signaling promoting the migration of invasive human carcinoma cells. Cancer Res 2001 Oct. 1; 61(19):7079–90.

FAK, overexpressed in several human cancers, induces survival, proliferation and motility of tumorogenic cells. Ben Mahdi M H, et al., Focal adhesion kinase regulation by oxidative stress in different cell types, IUBMB Life 2000; 50(4–5):291–9. Elevated FAK expression in human tumor cells has been correlated with an increased cell invasion potential. FAK activity plays a particular role in the progression of human carcinomas. Co-administration of DNA-methylation inhibitor in conjunction with one or more inhibitor(s) of member(s) of this family may be specifically advantageous in treatment of tumors of mesenchymal, neurological, and hematopoietic origin, particularly, in treatment of human carcinomas and metastasis-prone tumors.

f) Btk Family

Bruton's tyrosine kinase (Btk) family is characterized by having four structural modules: PH (pleckstrin homology) domain, SH3 (Src homology 3) domain, SH2 (Src homology 2) domain and kinase (Src homology 1) domain. They participate in signal transduction in response to virtually all types of extracellular stimuli that are transmitted by growth factor receptors, cytokine receptors, G-protein coupled receptors, antigen-receptors and integrins. Qiu Y., et al., Signaling network of the Btk family kinases, Oncogene 2000 Nov. 20;19(49):5651–61.

The examples of members of Btk family include, but are not limited to Btk/Atk, Itk/Emt/Tsk, Bmx/Etk, and Itk, Tec, Bmx, and Rlk. It is noted that these examples are present here for illustrative, rather then limiting purposes, so that other peptides that share structural and/or functional similarities with the members of Btk family are fall within the scope of this invention.

The examples of Btk inhibitors include, but are not limited to alpha-cyano-beta-hydroxy-beta-methyl-N-(2,5-dibromophenyl)propenamide (LFM-A 13). Uckun F M, et al., In vivo pharmacokinetic features, toxicity profile, and chemosensitizing activity of alpha-cyano-beta-hydroxy-beta- methyl-N-(2,5-dibromophenyl)propenamide (LFM-A13), a novel antileukemic agent targeting Bruton's tyrosine kinase. Clin Cancer Res 2002 May;8(5): 1224–33

Btk family members are essential for B cell development and B cell antigen receptor (BCR) function. The dysfunction of Btk family members is associated with tumors of hematopoietic origin, such as B-lineage leukemia or lymphoma. Inabe K, et al., Bruton's tyrosine kinase regulates B cell antigen receptor-mediated JNK1 response through Rac1 and phospholipase C-gamma2 activation. FEBS Lett 2002 Mar.

13;514(2–3):260–2. Co-administration of DNA-methylation inhibitor in conjunction with one or more inhibitor(s) of member(s) of this family may be specifically advantageous in the treatment of tumors of hematopoietic origin, particularly, in the treatment of B-lineage leukemia and lymphoma.

g) Syk/ZAP-70 Family

The non-receptor type of protein-tyrosine kinase Syk contains 2 Src homology 2 (SH2) domains in tandem and multiple autophosphorylation sites. Taniguchi, T., et al., Molecular cloning of a porcine gene Syk that encodes a 72-kDa protein-tyrosine kinase showing high susceptibility to proteolysis. J. Biol. Chem. 1991, 266, 15790–15796 Syk is activated upon binding of tandem SH2 domains to immunoreceptor tyrosine-based activating motif (ITAM) and plays an essential role in lymphocyte development and activation of immune cells. Sada K., et al., Structure and function of Syk protein-tyrosine kinase, J Biochem (Tokyo) 2001 August; 130(2): 177–86. Syk is critical for tyrosine phosphorylation of multiple proteins which regulate important pathways leading from the receptor, such as Ca (2+) mobilization and mitogen-activated protein kinase (MAPK) cascades.

Examples of members of Syk family include, but are not limited to Syk, Syk homologs, ZAP-70, and ZAP-70 homologs. It is noted that these examples are present here for illustrative, rather then limiting purposes, so that other peptides that share structural and/or functional similarities with the members of Syk family are fall within the scope of this invention.

Piceatannol (3,4,3',5'-tetrahydroxy-trans-stilbene) inhibits FceRI-mediated $IP_3$ production, serotonin secretion, membrane ruffling and cell spreading by inhibiting Syk Oliver, J. M, et al., Inhibition of mast cell FceRI-mediated signaling and effector function by the Syk-selective inhibitor, Piceatannol. J. Biol. Chem. 1994, 269, 29697–29703. FAK, Src, Jak1, rat PKC, and PKA, but not Lyn. Law, D. A, et al., (1999) Genetic and pharmacological analysis of Syk function in $a_{IIb}b_3$ signaling in platelets. Blood 93, 2645–2652. Wang, B. H., et al., (1998) Inhibition of eukaryote serine/threonine-specific protein kinases by piceatannol. Planta. Med. 64, 195–199. Su, L., et al., (2000) Distinct mechanisms of STAT phosphorylation via the interferon-a/b receptor. J. Biol. Chem. 275, 12661–12666. ER-27319 [3,4-dimethyl-10-(3-aminopropyl)-9-acridone oxalate] inhibits FceRI-mediated degranulation, tyrosine phosphorylation of Syk, but not Lyn in intact mast cells. Moriya, K., et al., (1997) ER-273 19, an acridone-related compound, inhibits release of antigen-induced allergic mediators from mast cells by selective inhibition of Fce receptor I-mediated activation of Syk. Proc. Natl. Acad. Sci. USA 94, 12539–12544. By screening more than 6 billion peptides, Phe-for-Tyr substituted version of ZAP-70 binding peptide, Lys-Leu-Ile-Leu-Phe-Leu-Leu-Leu was identified as a competitive inhibitor of ZAP-70. This peptide is a poor inhibitor of Lck and Syk. A membrane-permeant form of this peptide inhibits ZAP-70 in intact lymphocytes. Nishikawa, K., et al., (2000) A peptide library approach identifies a specific inhibitor for the ZAP-70 protein tyrosine kinase. Mol. Cell 6, 969–974

Recent findings reveal that expression of Syk appears to be involved in a wide variety of cellular functions and pathogenesis of malignant cancer. Syk expression is detected in breast tissue, benign breast tissue, and low-tumorigenic breast cancer. Dysfunction of ZAP-70 is associated with hematopoietic disorders. Sada K., et al., Structure and function of Syk protein-tyrosine kinase, J Biochem (Tokyo) 2001 August; 130(2): 177–86. Co-administration of DNA-methylation inhibitor in conjunction with one or more inhibitor(s) of member(s) of this family may be specifically advantageous in treatment of tumors mesenchymal origin, particularly, in treatment of breast cancer.

The inventors believe that a therapeutic combination of a DNA methylation inhibitor with one or more inhibitors that inhibit activity of TK may facilitate treatment of human cancers. The examples of inhibitors mentioned above include, but are not limited to chemical compounds, peptides, proteins, enzymes, antibodies and antisense fragment that may optionally be linked to enzymes. Optionally, the DNA methylation inhibitor that is used in conjunction with this invention is decitabine. Optionally, decitabine may be administered by inhalation and/or by injection.

II. Other Kinases and Diseases Associated with Their Activities i) Serine/Threonine Kinases According to the invention, a DNA methylation inhibitor such as decitabine may be combined with a serine/threonine kinase inhibitor for the treatment of diseases associated with the activity of the serine/threonine kinase. For example, the serine/threonine kinase may be a Raf kinase; and its inhibitor is BAY 43-9006. Lyons J F, et al. Endocr. Relat. Cancer. 2001 September;8(3):219–25.

The RAS RAF MEK ERK MAP kinase pathway mediates cellular responses to growth signals. Accumulation of mutations in the genes participating in this signaling pathway has led to onset and development of cancer. RAS is mutated to an oncogenic form in about 15% of human cancer, such as malignant melanoma. The three RAF genes code for cytoplasmic serine/threonine kinases that are regulated by binding RAS. For BRAF there are somatic missense mutations in 66% of malignant melanomas and at lower frequency in a wide range of human cancers. All mutations are within the kinase domain, with a single substitution (V599E) accounting for 80%. Mutated BRAF proteins have elevated kinase activity and are transforming in NIH3T3 cells. Furthermore, RAS function is not required for the growth of cancer cell lines with the V599E mutation. Davies H, et al. Nature 2002 July;417(6892):949–54 Mutations of the BRAF gene in human cancer.

ii) Protein Kinase Kinase

According to the invention, a DNA methylation inhibitor such as decitabine may be combined with a protein kinase kinase inhibitor for the treatment of diseases associated with the activity of the protein kinase kinase. For example, the protein kinase kinase may be a Raf-mitogen-activated protein kinase kinase (MEK) or a protein kinase B (Akt) kinase.

It is believed that activation of cell survival pathways, such as the Raf-mitogen-activated protein kinase kinase (MEK)-extracellular signal-regulated kinase (ERK) pathway, results in inhibition apoptosis. MacKeigan J P, et al. Clin Cancer Res 2002 July;8(7):2091–9. Thus, treatment with a combination of decitabine and ERK inhibitor would enhance apoptosis of cancer cells, thereby achieving higher therapeutic efficacy. In addition, inhibition of MEK with a MEK inhibitor may also lead to inactivation of the antiapoptotic Akt (protein kinase B) kinase.

iii) Extracellular Signal-Regulated Kinase (ERK)

According to the invention, a DNA methylation inhibitor such as decitabine may be combined with an ERK inhibitor for the treatment of diseases associated with the activity of the ERK. Examples of the inhibitor of ERK include but are not limited to PD98059, PD184352, and U0126.

Serum and growth factors activate both the canonical ERK1/2 pathway and the ERK5/BMK1 pathway. It has been found that pharmacological inhibition of the ERK1/2 pathway using PD98059 and U0126 prevented cyclin D1 expression and inhibits cell proliferation, suggesting that the ERK1/2 pathway is rate limiting for cell cycle re-entry. Both PD98059 and U0126 also inhibited the ERK5/BMK1 pathway raising the possibility that the anti-proliferative effect of such drugs may be due to inhibition of ERK5 or both pathways. However, serum-stimulated DNA synthesis and cyclin D1 expression was inhibited by low doses of PD184352, which abolished ERK1 activity but had no effect on ERK5. Similarly, in cycling cells PD 184352 caused a dose-dependent $G_1$ arrest and inhibition of cyclin D1 expression at low doses, which inhibited ERK1 but were without effect on ERK5. Squires M S, et al. Biochem J 2002 Jun. 17.

iii) Phosphatidylinositol 3'-kinase (PI3K)

According to the invention, a DNA methylation inhibitor such as decitabine may be combined with a PI3K inhibitor for the treatment of diseases associated with the activity of the PI3K. Examples of the inhibitor of ERK include but are not limited to LY294002 (Bacus S S, et al. Oncogene 2002 21(22):3532–40). LY294002 has been shown to potently and selectively inhibit PI3K activity in animal model of ovarian cancer. Hu, L. et al. Cancer Res 2002 Feb. 15;62(4): 1087–92.

Phosphorylated lipids are produced at cellular membranes during signaling events and contribute to the recruitment and activation of various signaling components. PI3K catalyzes the production of phosphatidylinositol-3,4,5-trisphosphate and participates in cell survival pathways, regulation of gene expression and cell metabolism, and cytoskeletal rearrangements. The PI3K pathway is implicated in human diseases including diabetes and cancer. Cantley L C. Science 2002, 296(5573):1655–7. It has been observed that PI3K/AKT signaling augments resistance to stress-induced apoptosis in breast cancer cells overexpressing HER-2/neu. Bacus S S, et al. Oncogene 2002 21(22):3532–40. It is believed that a combination of decitabine and a PI3K inhibitor such as LY294002 would reduce the resistance to apoptosis in breast and ovarian cancer and thus lead to a more efficacious treatment of theses popular diseases among women.

4. Routes of Delivery, Formulations and Kits

The DNA methylation inhibitor employed in the present invention may be administered or co-administered in any conventional dosage form. For example, the inhibitor be administered or co-administered parenterally, orally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, or intrathecally.

In a preferred embodiment, decitabine is administrated to a patient by injection, including intravenous or subcutaneous injection, such as bolus intravenous injection, continuous intravenous infusion and intravenous infusion over 1 hour. For example, decitabine may administered into the patient via an 1–24 hour intravenous infusion per day for 3–5 days per treatment cycle at a dose preferably ranging from 1–100 $mg/m^2$, more preferably ranging from 2–50 $mg/m^2$, and most preferably from 5–20 $mg/m^2$. The preferred dosage below 50 $mg/m^2$ for decitabine is considered to be much lower than that used in conventional chemotherapy for cancer.

In another embodiment, decitabine is administered via intravenous infusion at a dose ranging from 1 to 100 $mg/m^2$ per day for at least 3 days per treatment cycle. In yet another embodiment, decitabine is administered via intravenous infusion at a dose ranging from 5 to 20 $mg/m^2$ for 1 hour per day for 5 consecutive days for 2 weeks per treatment cycle.

In yet another embodiment, decitabine is administered to the patient subcutaneously at a dose ranging from 0.01 to 1 mg/Kg, optionally at a dose ranging from 0.1 to 0.5 mg/Kg at least once a week for at least 4 weeks, optionally at a dose ranging from 0.1 to 0.3 mg/Kg twice a week for at least 4 weeks, and optionally at a dose of 0.2 mg/Kg twice a week for 6 weeks, drug-free for two weeks, and then at a dose of 0.2 mg/Kg twice a week until the clinical endpoint(s) is achieved.

The DNA methylation inhibitors employed in the invention may also be administered or co-administered in slow release dosage forms. Furthermore, the DNA methylation inhibitors may be administered or co-administered with conventional pharmaceutical excipients and additives.

Decitabine may be supplied as sterile powder for injection, together with buffering salt such as potassium dihydrogen and pH modifier such as sodium hydroxide. This formulation is preferably stored at 2–8° C., which should keep the drug stable for at least 2 years. This powder formulation may be reconstituted with 10 ml of sterile water for injection. This solution may be further diluted with infusion fluid known in the art, such as 0.9% sodium chloride injection, 5% dextrose injection and lactated ringer's injection. It is preferred that the reconstituted and diluted solutions be used within 4–6 hours for delivery of maximum potency.

In another embodiment, decitabine may be administered by inhalation in various forms including, but not limited to powdered aerosol, liquid aerosol, and mist. In one variation, aerosol, may be created by any of a number of known methods (for example, by vaporization, nebulization, electrospraying, expansion through an orifice, and the like) and may have an electrical charge or not. Optionally, propellants, such as a halocarbon propellant, trichloromonofluoromethane, and dichlorodifluoromethane may be employed to facilitate delivery of aerosoled decitabine.

The inventive combination of DNA methylation inhibitor and imatinib mesylate may be used in the form of kits. The arrangement and construction of such kits is conventionally known to one of skill in the art. Such kits may include containers for containing the inventive combination of therapeutic agents and/or compositions, and/or other apparatus for administering the inventive combination of therapeutic agents and/or compositions.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents. Additionally, the above examples are provided for the purpose of illustrating the claimed invention, and should not be construed so as to limit the scope of the claimed invention.

What is claimed is:

1. A method for treating a patient having a disease selected from the group consisting of inflammation, benign tumors, malignant tumors, leukemia, asthma, allergy-associated chronic rhinitis, autoimmune diseases and mastolocytosis, comprising:
   administering decitabine to the patient in therapeutically effective amount; and
   administering a tyrosine kinase inhibitor to the patient in therapeutically effective amount, such that the in viva activity of the tyrosine kinase is reduced relative to that prior to the treatment, wherein said tyrosine kinase is an epidermal growth factor receptor.

2. The method of claim 1, wherein the decitabine is administered orally, parenterally, intraperitoneally, intravenously, intraarterially, transdermally, sublingually, subcutaneously, intramuscularly, rectally, transbuccally, intranasally, liposomally, via inhalation, vaginally, intraoccularly, via local delivery, subcutaneously, intraadiposally, intraarticularly, or intrathecally.

3. The method of claim 1, wherein the decitabine is administered intravenously, subcutaneously, intramuscularly, orally or via inhalation.

4. The method of claim 1, wherein the tyrosine kinase inhibitor is administered orally, parenterally, intraperitoneally, intravenously, intraarterially, transdermally, sublingually, intramuscularly, rectally, transbuccally, intranasally, liposomally, via inhalation, vaginally, intraoccularly, via local delivery, subcutaneously, intraadiposally, intraarticularly, or intrathecally.

5. The method of claim 1, wherein the epidermal growth factor receptor is selected from the group consisting of HER1, HER2/neu, HER3, and HER4.

6. The method of claim 5, wherein the inhibitor of the epidermal growth factor receptor is selected from the group consisting of trastuzumab, gefitinib, PD168393, CI1033, IMC-C225, EKB-569, and an inhibitor binding covalently to Cys residues of the receptor tyrosine kinase.

7. The method of claim 5, wherein the disease is selected from the group consisting of epithelial tumor, carcinoma of upper aerodigestive tract, lung cancer, and non-small cell lung cancer.

8. The method of claim 1, wherein the decitabine and the epidermal growth factor receptor inhibitors are co-administered in therapeutically synergistic amounts.

9. The method of claim 1, wherein the decitabine is administered intravenously or subcutaneously.

10. The method of claim 9, wherein decitabine is administered to the patient via an intravenous infusion at a dose ranging from 1 to 100 mg/m$^2$ per day.

11. The method of claim 9, wherein decitabine is administered to the patient via an intravenous infusion at a dose ranging from 2 to 50 mg/m$^2$ per day.

12. The method of claim 9, wherein decitabine is administered to the patient via an intravenous infusion at a dose ranging from 5 to 20 mg/m$^2$ per day.

13. The method of claim 9, wherein decitabine is administered to the patient via an intravenous infusion for at least 3 days per treatment cycle at a dose ranging from 1 to 100 mg/m$^2$ per day.

14. The method of claim 9, wherein decitabine is administered to the patient subcutaneously at a dose ranging from 0.01 to 1 mg/Kg.

15. The method of claim 9, wherein decitabine is administered to the patient subcutaneously at a dose ranging from 0.1 to 0.5 mg/Kg at least once a week for at least 4 weeks.

16. The method of claim 9, wherein decitabine is administered to the patient subcutaneously at a dose ranging from 0.1 to 0.3 mg/Kg twice a week for at least 4 weeks.

17. A method for treating a patient having a disease selected from the group consisting of inflammation, benign tumors, malignant tumors, leukemia, asthma, allergy-associated chronic rhinitis, autoimmune diseases and mastolocytosis, comprising:
   administering decitabine to the patient in therapeutically effective amount; and
   administering a kinase inhibitor to the patient in therapeutically effective amount, such that the in vivo activity of the kinase is reduced relative to that prior to the treatment wherein said kinase is an epidermal growth factor receptor.

18. The method of claim 17, wherein the decitabine is administered orally, parenterally, intraperitoneally, intravenously, intraarterially, transdermally, sublingually, intramuscularly, rectally, transbuccally, intranasally, liposomally, via inhalation, vaginally, intraoccularly, via local delivery, subcutaneously, intraadiposally, intraarticularly, or intrathecally.

19. The method of claim 17, wherein the decitabine and is administered intravenously, intramuscularly, subcutaneously, orally or via inhalation.

20. The method of claim 17 wherein the disease associated with abnormal activity of the kinase is selected from the group consisting of epithelial tumor, carcinoma of upper aerodigestive tract, lung cancer, and non-small cell lung cancer.

* * * * *